US00PP24265P2

(12) United States Plant Patent
Gitzels

(10) Patent No.: US PP24,265 P2
(45) Date of Patent: Feb. 25, 2014

(54) *DAHLIA* PLANT NAMED 'DAPAMAR'

(50) Latin Name: *Dahlia variabilis*
Varietal Denomination: Dapamar

(75) Inventor: Jeroen Gitzels, Hoorn (NL)

(73) Assignee: Ball Horticultural Company, West Chicago, IL (US)

( * ) Notice: Subject to any disclaimer, the term of this patent is extended or adjusted under 35 U.S.C. 154(b) by 60 days.

(21) Appl. No.: 13/507,109

(22) Filed: Jun. 5, 2012

(51) Int. Cl.
*A01H 5/00* (2006.01)

(52) U.S. Cl.
USPC ..... Plt./321

(58) Field of Classification Search
USPC ..... Plt./321
See application file for complete search history.

*Primary Examiner* — Annette Para
(74) *Attorney, Agent, or Firm* — Audrey Charles

(57) ABSTRACT

A new and distinct cultivar of *Dahlia* plant named 'Dapamar', characterized by its double-type, medium red and yellow bicolored flowers, medium green-colored foliage, and moderately vigorous, compact-upright growth habit, is disclosed.

1 Drawing Sheet

Latin name of genus and species of plant claimed: *Dahlia variabilis*.

Variety denomination: 'Dapamar'.

BACKGROUND OF THE INVENTION

The present invention relates to a new and distinct cultivar of *Dahlia* plant botanically known as *Dahlia variabilis* and hereinafter referred to by the cultivar name 'Dapamar'.

The new cultivar originated in a controlled breeding program in Rijsenhout, The Netherlands during October 2005. The objective of the breeding program was the development of *Dahlia* cultivars that are freely flowering with large flowers and a moderately vigorous, compact-upright growth habit.

The new *Dahlia* cultivar is the result of open-pollination. The female (seed) parent of the new cultivar is the proprietary *Dahlia variabilis* breeding selection designated 1253, not patented, characterized by its double-type, medium red-colored flowers, medium green-colored foliage, and moderately vigorous, compact-upright growth habit. The male (pollen) parent of the new cultivar is unknown. The new cultivar was discovered and selected as a single flowering plant within the progeny of the above stated open-pollination during September 2006 in a controlled environment in Rijsenhout, The Netherlands.

Asexual reproduction of the new cultivar by terminal stem cuttings since September 2006 in Rijsenhout, The Netherlands and West Chicago, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Dapamar' as a new and distinct cultivar of *Dahlia* plant:

1. Double-type, medium red and yellow bicolored flowers;
2. Medium green-colored foliage; and
3. Moderately vigorous, compact-upright growth habit.

Plants of the new cultivar differ from plants of the female parent primarily in flower color. The female parent is not yellow bicolored.

Of the many commercially available *Dahlia* cultivars, the most similar in comparison to the new cultivar is 'Balnovapse', not patented. However, in side by side comparisons, plants of the new cultivar differ from plants of 'Balnovapse' in at least the following characteristics:

1. Plants of the new cultivar are at least two weeks earlier to flower than plants of 'Balnovapse';
2. Plants of the new cultivar have a darker red and lighter yellow ray floret color than plants of 'Balnovapse'; and
3. Plants of the new cultivar have the ray floret yellow coloration located at the base of the ray florets, while the yellow coloration is in a streaked pattern on the ray florets of 'Balnovapse'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Dapamar'. The plants were grown in 4-inch pots for 7 weeks in a greenhouse in West Chicago, Ill.

DETAILED BOTANICAL DESCRIPTION

Figure 1:
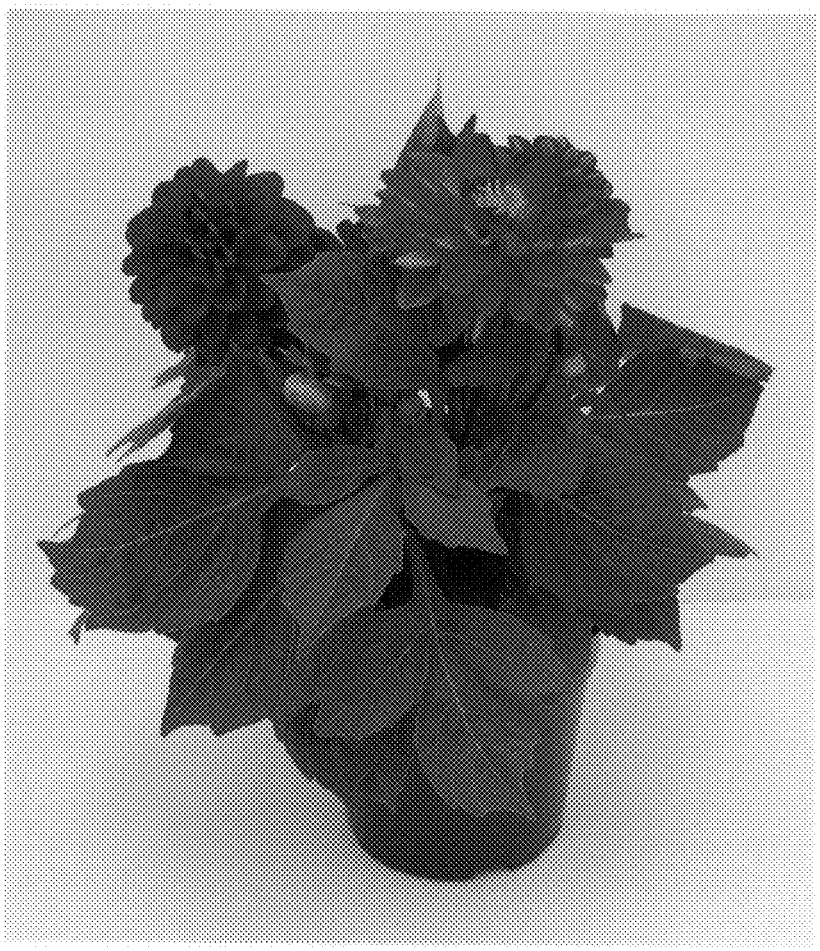
FIG. 1 illustrates a side view of the overall growth and flowering habit of 'Dapamar'.
Figure 2:
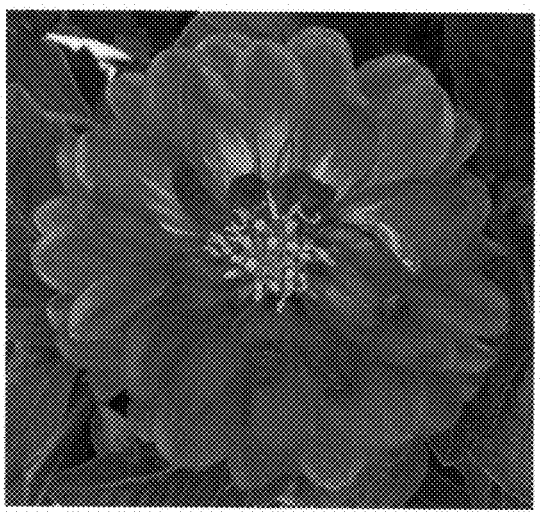
FIG. 2 illustrates a close-up view of an individual inflorescence of 'Dapamar'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2007 edition, except where general color terms of ordinary significance are used. The color values were determined in April 2012 under natural light conditions in West Chicago, Ill.

The following descriptions and measurements describe plants produced from cuttings from stock plants and grown in a glass-covered greenhouse under conditions comparable to those used in commercial practice. The plants were grown in West Chicago, Ill. in 4-inch pots for 7 weeks utilizing a soilless growth medium. Greenhouse temperatures were maintained at approximately 70° F. to 77° F. (21° C. to 25° C.) during the day and approximately 65° F. to 68° F. (18° C. to 20° C.) during the night. Greenhouse light levels of 2,500 footcandles to 6,000 footcandles were maintained during the day. Measurements and numerical values represent averages of typical plants.

Botanical classification: *Dahlia variabilis* cultivar Dapamar.

Parentage:

*Female parent.*—Proprietary *Dahlia variabilis* breeding selection designated 1253, not patented.

*Male parent.*—Unknown.

Propagation:

*Type cutting.*—Terminal stem.

*Time to initiate roots.*—Approximately 7 to 10 days.

*Time to produce a rooted cutting.*—Approximately 28 to 32 days.

*Root description.*—Fine, fibrous.

*Rooting habit.*—Freely branching.

*Tuber formation.*—Will form under short day conditions of at least 13 to 14 hours of darkness.

Plant description:

*Commercial crop time.*—Approximately 6 to 8 weeks from a rooted cutting to finish in a 10 cm pot.

*Growth habit and general appearance.*—Moderately vigorous, compact-upright.

*Size.*—Height from soil level to top of plant plane: Approximately 16.1 cm. Height from soil level to top of foliage: Approximately 14.0 cm. Width: Approximately 17.7 cm.

*Branch.*—Quantity of lateral branches per plant: Approximately 8. Strength: Moderately strong. Length of lateral branch: Approximately 7.9 cm. Diameter of lateral branch at central internode: Approximately 4.0 mm. Texture: Glabrous. Color: 144A with an overlay of 187A. Length of central internode of lateral branch: Approximately 1.7 cm.

Foliage description:

*General description.*—Quantity of leaves per lateral branch: Approximately 6. Type: Simple. Quantity of leaflets per compound leaf: Approximately 3. Fragrance: None. Arrangement: Opposite. Aspect: Petiole is acute angle to stem; blade is perpendicular to stem. Shape of leaf and leaflet: Elliptic. Margin of leaf and leaflet: Widely serrate. Apex of leaf and leaflet: Acute. Base of leaf and leaflet: Attenuate. Venation pattern: Pinnate.

*Simple leaf.*—Length: Approximately 7.6 cm. Width: Approximately 5.4 cm. Texture of upper and lower surfaces: Sparsely pubescent on venation. Color of upper surface: Closest to N137A and venation of 146B with an overlay of 187B on midvein. Color of lower surface: Closest to 191A and venation of 146B with a faint overlay of 187B on midvein. Length of petiole: Approximately 2.6 cm. Diameter of petiole: Approximately 4.0 mm. Texture of upper and lower surfaces of petiole: Glabrous. Color of upper surface of petiole: 146B with a faint overlay of 187B. Color of lower surface of petiole: 146B.

*Mature trifoliate leaf.*—Length of mature trifoliate leaf: Approximately 7.9 cm. Width of mature trifoliate leaf: Approximately 8.2 cm. Length of terminal leaflet: Approximately 6.0 cm. Width of terminal leaflet: Approximately 3.9 cm. Length of lateral leaflet: Approximately 4.6 cm. Width of lateral leaflet: Approximately 2.8 cm. Texture of upper and lower surfaces: Sparsely pubescent on venation. Color of upper surface: Closest to N137A and venation of 146B with an overlay of 187B on midvein. Color of lower surface: Closest to 191A and venation of 146B with a faint overlay of 187B on midvein. Length of petiole of mature trifoliate leaf: Approximately 3.0 cm. Diameter of petiole of mature trifoliate leaf: Approximately 4.0 mm. Texture of upper and lower surfaces of petiole of mature trifoliate leaf: Glabrous. Color of upper and lower surfaces of petiole of mature trifoliate leaf: 146B with a faint overlay of 187B Length of rachis: Approximately 8.0 mm. Diameter of rachis: Approximately 3.0 mm. Texture of upper and lower surfaces of rachis: Glabrous. Color of upper and lower surfaces of rachis: 146B with a faint overlay of 187B.

Flowering description:

*Flowering habit.*—'Dapamar' is freely flowering under outdoor growing conditions with substantially continuous blooming from spring through autumn and year round in the greenhouse environment.

*Lastingness of individual inflorescence on the plant.*—Approximately 2 weeks.

Inflorescence description:

*General description.*—Type: Composite, daisy-eyed double, persistent. Aspect: Facing upward and outward. Arrangement: Terminal, arising from leaf axils on strong peduncles positioned over the foliage. Disc and ray florets arranged acropetally on a capitulum. Quantity per plant: Approximately 3. Fragrance: None. Shape: Hemispherical when ray florets are fully open. Inflorescence diameter: Approximately 6.0 cm. Inflorescence depth: Approximately 3.0 cm. Disc diameter: Approximately 1.1 cm. Receptacle diameter at base: Approximately 6.0 mm. Receptacle depth: Approximately 2.0 mm. Receptacle color: 150C.

*Peduncle.*—Strength: Strong. Aspect: Erect. Length: Approximately 7.0 cm. Diameter: Approximately 3.0 mm. Texture: Glabrous. Color: 144A with an overlay of 187A.

*Bud.*—Rate of bud opening: Generally takes 2 weeks for bud to progress from first color to fully open flower. Quantity per plant: Approximately 2.

*Bud just before opening.*—Shape: Oblate. Depth at first color: Approximately 1.4 cm. Diameter at first color: Approximately 1.5 cm. Texture: Glabrous. Color: Outer surface of the phyllaries is 154B with 144B at base, petals of 46B with 2B at tip.

*Ray florets.*—Quantity per inflorescence: Approximately 72. Arrangement: Imbricate, in multiple whorls. Aspect: Cupped. Shape: Ovate. Margin: Entire. Apex: Acuminate to obtuse. Base: Fused into a short corolla tube. Appearance: Dull. Length: Approximately 2.6 cm. Width: Approximately 1.4 cm. Texture of upper surface: Glabrous. Texture of lower surface: Sparsely pubescent, ribbed. Color of upper surface when first and fully open: 46A with base of 2A. Color of lower surface when first and fully open: 2C with a mixture of 46A and 46B at apex. Color of upper surface before senescence: 53A with base of 2A. Color of lower surface before senescence: 2B with a mixture of 46A and 53A at apex.

*Disc florets.*—Quantity per inflorescence: Approximately 31. Arrangement: Massed in center of inflorescence. Aspect: Erect. Shape: Tubular. Margin: Entire. Apex: 5 acute tips. Base: Fused. Length: Approximately 1.3 cm. Diameter at apex: Approximately 2.0 mm. Diameter at base: Approximately 1.0 mm. Texture: Glabrous. Color when fully open: 1A, translucent.

*Outer phyllaries.*—Quantity: Approximately 5 to 6. Aspect: Flat. Shape: Rhombic. Margin: Entire. Apex: Broadly acute. Base: Truncate. Length: Approximately 1.4 cm. Width: Approximately 6.0 mm. Texture of upper and lower surfaces: Glabrous. Color of upper surface: 137A. Color of lower surface: 138A.

*Inner phyllaries.*—Quantity: Approximately 1 per floret. Shape: Linear, imbricate. Margin: Entire. Apex: Broadly acute. Base: Truncate. Length of outermost: Approximately 1.4 cm. Width of outermost: Approximately 5.0 mm. Length of innermost: Approximately 9.0 mm. Width of innermost: Approximately 3.0 mm. Texture of upper and lower surfaces: Glabrous. Color of upper and lower surfaces: 154B, translucent with 143A at base of outermost.

*Reproductive organs.*—Androecium: On disc florets. Stamen quantity: 5 per floret. Stamen length: Approximately 7.0 mm. Anther shape: Linear. Anther length: Approximately 3.0 mm. Anther color: 1A, translucent. Pollen amount: Abundant. Pollen color: 21A. Gynoecium: On disc and ray florets. Pistil length: Approximately 1.3 cm. Stigma shape: 2 branched. Stigma length: Approximately 3.0 mm. Stigma color: 21A. Style length: Approximately 8.0 mm. Style color: 1A, translucent. Ovary length: Approximately 2.0 mm. Ovary color: 145D.

Seed and fruit production: Neither seed nor fruit production has been observed.

Disease and pest resistance: Resistance to pathogens and pests common to *Dahlia* has not been observed.

What is claimed is:

1. A new and distinct cultivar of *Dahlia* plant named 'Dapamar', substantially as herein shown and described.

* * * * *